United States Patent [19]

Burton et al.

[11] 3,957,773

[45] May 18, 1976

[54] PROCESS FOR PREPARING CEPHALOSPORIN COMPOUNDS FROM 7-ADCA

[75] Inventors: Brian Burton, Ruislip; William Graham, Gerrards Cross, both of England

[73] Assignee: Glaxo Laboratories Limited, Greenford, England

[22] Filed: July 2, 1974

[21] Appl. No.: 485,236

[30] Foreign Application Priority Data

July 5, 1973 United Kingdom............... 32111/73

[52] U.S. Cl............................ 260/243 C; 424/246
[51] Int. Cl.$^2$........................................ C07D 501/06
[58] Field of Search ................................ 260/243 C

[56] References Cited
UNITED STATES PATENTS

| | | |
|---|---|---|
| 3,694,437 | 9/1972 | Jackson........................... 260/243 C |
| 3,743,644 | 7/1973 | Essery et al...................... 260/243 C |
| 3,769,280 | 10/1973 | Parker............................. 260/243 C |
| 3,809,699 | 5/1974 | Ishimaru.......................... 260/243 C |
| 3,843,639 | 10/1974 | Sapino et al..................... 260/243 C |

*Primary Examiner*—Nicholas S. Rizzo
*Attorney, Agent, or Firm*—Bacon & Thomas

[57] ABSTRACT

7β-Amino-3-methylceph-3-em-4-carboxylic acid is converted to cephalexin in high yield and relatively uncontaminated with unreacted 7β-amino-3-methylceph-3-em-4-carboxylic acid if it is silylated prior to acylation with phenyl glycyl chloride hydrochloride and if the acylation reaction is conducted in dimethylformamide at low temperature in the presence of certain weak tertiary nitrogen bases.

7 Claims, No Drawings

PROCESS FOR PREPARING CEPHALOSPORIN COMPOUNDS FROM 7-ADCA

This invention concerns improvements in or relating to cephalosporin compounds and is particularly concerned with a process for the preparation of cephalexin. More particularly the invention is concerned with an improved process for the preparation of cephalexin from 7β-amino-3-methylceph-3-em-4-carboxylic acid, sometimes referred to as 7-aminodesacetoxycephalosporanic acid or, more simply, 7-ADCA.

Cephalexin [7β-(D-2-amino-2-phenylacetamido)-3-methylceph-3-em-4-carboxylic acid] is well known as a valuable orally-administrable cephalosporin antibiotic and may be prepared by acylation of 7-ADCA or a carboxylate derivative, e.g. a salt or ester, thereof to introduce the D-α-aminophenylacetyl group at the 7-position, followed if necessary by de-esterification. 7-ADCA or the carboxylate derivative thereof employed as starting material may itself conveniently be obtained from a fermentation-produced penicillin compound, e.g. penicillin G or penicillin V, by methods involving ring expansion of a penicillin sulphoxide ester, for example as described in British Patent Specifications Nos. 1,299,734; 1,312,232 or 1,312,233 and subsequent N-deacylation (and de-esterification) of the resulting 7β-acylamido-3-methylceph-3-em-4-carboxylate ester, the deacylation being effected by, for example, the imide halide technique described in U.S. Patent No. 3,697,515 and British Patent Specifications Nos. 1,241,655 and 1,227,014.

Existing industrial processes for the manufacture of cephalexin generally employ acylating agents such as D-phenylglycyl chloride as their N-protected derivatives, e.g. derivatives wherein the amino group is protected by substitution with a hydrolytically cleavable protecting group such as t-butoxy-carbonyl or a reductively cleavable protecting group such as 2,2,2-trichloroethoxycarbonyl, in order to minimise undesirable side reactions involving the amino group during the acylation reaction. Where such acylating agents are employed, subsequent N-deprotection reactions are necessary in order to regenerate the amino group in the cephalexin 7-position side chain, and such subsequent reactions necessarily complicate a preparative sequence and add to its overall cost.

Accordingly, it would be advantageous in the manufacture of cephalexin to use acylating agents in acid addition salt form, e.g. D-phenylglycyl chloride hydrochloride, since the protonated amino group in such reagents is effectively deactivated against side reactions and since the need for a specific N-deprotection step after acylation would be obviated. This avoidance of a specific N-deprotection step is especially advantageous in the preparation of cephalexin by acylation of 7-ADCA (rather than an ester thereof). When manufacturing cephalexin from 7-ADCA and for example, phenyl glycyl chloride hydrochloride, no subsequent deprotection step(s) is necessary to regenerate the 4-carboxy group or the side chain amino group thus minimising the number of reactions required to produce the desired end product.

The reaction of 7-ADCA with acylating agents such as phenylglycyl chloride hydrochloride does, however, give rise to a number of problems. Thus, using conventional acylation techniques, e.g. reaction in an organic solvent in the presence of a hydrogen halide binding agent the reaction in many cases does not go to completion, so that the cephalexin product is contaminated with unreacted 7-ADCA or obtained in low yield. Phenylglycyl chloride hydrochloride also tends to promote a variety of unwanted side reactions including conversion into phenylglycine and coupling with other species present to give products such as phenylglycylcephalexin and phenylglycylphenylglycine, these further contaminating the desired end-product. Thus the yields of cephalexin are generally low and several separation and/or purification steps are often necessary to obtain acceptably pure cephalexin for pharmaceutical use, so that such processes are generally not economically viable in the industrial manufacture of cephalexin.

We have now found, however, that 7-ADCA may be converted to cephalexin in high yield and relatively uncontaminated with unreacted 7-ADCA if the 7-ADCA is silylated prior to acylation with phenyl glycyl chloride hydrochloride and if the acylation reaction is conducted in dimethylformamide at low temperature in the presence of certain weak tertiary nitrogen bases. The cephalexin so produced is then separated, after subsequent desilylation during work-up procedures, as a bis-dimethylformamide solvate; this solvate is substantially uncontaminated by, for example, byproducts derived from phenylglycyl chloride hydrochloride, and may be converted directly, without further purification steps, to a pharmaceutical grade cephalexin product such as the hydrate. The simplicity of this process coupled with the high yields of substantially pure cephalexin which may be obtained render the process of considerable value in the industrial manufacture of cephalexin.

Thus according to one aspect of the present invention we provide a process for the preparation of a bis-dimethylformamide solvate of cephalexin which comprises (a) acylating a silylated derivative of 7-ADCA by reaction with phenylglycyl chloride hydrochloride in dimethylformamide at a temperature not exceeding 0°C, preferably in the range −20° to −40°C, in the presence of a tertiary nitrogen base having a pKa in the range 3.0 − 7.0, preferably in the range 4.5 − 5.5, (b) precipitating the cephalexin product so formed as a bis-dimethylformamide solvate by diluting the reaction solution with water and adjusting the pH to about 6.9 by addition of a base, if necessary after separation of any insoluble material present, with consequent removal of any silyl groups present in the said cephalexin product, and, if desired, (c) isolating cephalexin from the said bis-dimethylformamide solvate.

Bases which may be used in step (a) include aromatic heterocyclic bases such as pyridine, quinoline and homo logues and/or substituted derivatives thereof, for example α-, β- and γ-picoline, methyl isonicotinate or quinaldine; and N,N-disubstituted anilines, for example N,N-dimethylaniline or N,N- diethylaniline. We especially prefer to use pyridine as the tertiary nitrogen base, acylations employing pyridine preferably being conducted at temperatures below −20°C, e.g. at about −30°C. In general the optimum reaction temperature for acylation in the presence of a particular base may be determined by empirical methods.

A wide range of silylated derivatives of 7-ADCA may be used in the acylation step and these may be prepared by any convenient method. Advantageously the silylating agent is a halosilane or a silazane, e.g. a compound having one of the formulae $R_3SiX$; $R_2SiX_2$; $R_3Si.NR_2$; $R_3Si.NH\ SiR_3$; $R_3Si.NH.COR$; $R_3Si.NH.CO.NH.SiR_3$;

R₃Si.NH.CO.NR.SiR₃ or RC(OSiR₃):NSiR₃ where X is a halogen atom, e.g. a chlorine atom, and the various groups R, which may be the same or different, represent hydrogen atoms or alkyl, e.g. methyl, ethyl, n-propyl, isopropyl; aryl, e.g. phenyl; or aralkyl, e.g. benzyl, groups. Some of these compounds may not be particularly stable under the reaction conditions where R is hydrogen for all R groups, and it is generally preferred that all the groups R are hydrocarbon groups. Preferred hydrocarbon groups R are methyl and phenyl, as in, for example, hexamethyldisilazane [(Me₃Si)₂ NH]. Further useful silylating agents are the compounds of formula (R¹O)₂SiX₂ and

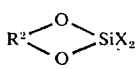

where R¹ is a lower (e.g. C₁₋₆)alkyl group, R² is a lower (e.g. C₂₋₄) alkylene group and X is as defined above.

Examples of suitable silylating agents are trimethyl chlorosilane, hexamethyldisilazane, triethyl chlorosilane, methyl trichlorosilane, dimethyl dichlorosilane, triethyl bromosilane, tri-n-propyl chlorosilane, bromomethyl dimethyl chlorosilane, tri-n-butyl chlorosilane, methyl diethyl chlorosilane, dimethyl ethyl chlorosilane, phenyl dimethyl bromosilane, benzyl methyl ethyl chlorosilane, phenyl ethyl methyl chlorosilane, triphenyl chlorosilane, tri-o-tolyl chlorosilane, tri-p-dimethylaminophenyl chlorosilane, N-ethyl triethylsilylamine, hexaethyldisilazane, triphenyl silylamine, tri-n-propyl silylamine, tetraethyl dimethyl disilazane, tetramethyl diethyl disilazane, tetramethyl diphenyl disilazane, hexaphenyldisilazane, hexa-p-tolyl disilazane, N,O-bis-trimethylsilylacetamide, N-trimethylsilylacetamide, N-(triphenylsilyl)ethylcarbamate, N-(triethylsilyl)urea, dimethoxydichlorosilane, diethoxydichlorosilane and dichloropropylenedioxysilane.

In general we prefer to use about two equivalents of the silylating agent relative to the quantity of 7-ADCA to be silylated, so that an O,N-bis silylated derivative is produced.

Where a silyl halide is employed as the silylating agent, the silylation may be conducted in an inert organic solvent such as benzene, toluene, dimethylformamide, methylene chloride, ethylene chloride, tetrahydrofuran or acetonitrile, in the presence of a nitrogen base such as, for example, triethylamine, dimethylaniline, quinoline, lutidine or pyridine, the base serving as a hydrogen halide acceptor; the amount of nitrogen base employed is preferably substantially equivalent to the quantity of silyl halide used. Thereafter the resulting silylated derivative may be isolated, for example by evaporation of the solvent. Where a silazane is employed as the silylating agent, the silylation is conveniently effected by heating the silazane and 7-ADCA so that ammonia or amine derivatives formed as by products of the reaction are distilled off.

Silylated derivatives of 7-ADCA so obtained may be acylated in accordance with the invention by, for example, dissolving the derivative in dimethylformamide, adding the tertiary nitrogen base and adjusting the temperature of the solution to the desired value, and, finally, adding phenylglycyl chloride hydrochloride, advantageously with stirring of the reaction system. The phenylglycyl chloride hydrochloride may, if desired, be added in portions over a period of time.

According to a preferred embodiment of the invention, however, a dimethylformamide solution or suspension of 7-ADCA is silylated by reaction with a silyl halide such as trimethylchlorosilane and the resulting silylated 7-ADCA derivative is acylated directly in the same solution, without any intermediate separation. Silylation and acylation in accordance with this embodiment renders the overall process particularly simple and convenient since, for example, avoidance of the need to change the solvent after silylation significantly reduces plant requirements and operational costs. Thus in such a process it is simply necessary after silylation to add the tertiary nitrogen base to the dimethylformamide solution, adjust the temperature and add phenylglycyl chloride hydrochloride. Again it is preferred to stir the reaction system during this last addition at least, and again portionwise addition of phenylglycyl chloride hydrochloride may be employed.

Where a hydrogen halide binding agent is employed during silylation, any resulting insoluble salts may, if desired, be separated, e.g. by filtration or centrifugation, prior to acylation. Thus, for example, in processes where the solvent is to be removed and replaced by dimethylformamide after silylation such salts may be filtered off before removal of the solvent, while in cases where dimethylformamide is employed as solvent throughout the process such salts may be separated before addition of the tertiary nitrogen base and phenylglycyl chloride hydrochloride.

Where an excess of a strong base such as triethylamine is employed as hydrogen halide binding agent in the silylation reaction it may be desirable to neutralise any residual strong base before acylation of the silylated 7-ADCA derivative, since such residual strong base might otherwise interfere in the acylation reaction. Any residual strong base is conveniently neutralised by adding a mineral acid salt of a weak nitrogen base (e.g. having a pKa not exceeding 7.0) to the reaction system before addition of phenylglycyl chloride hydrochloride, an example of a suitable salt for this purpose being quinoline hydrochloride. In cases where the solvent is changed after silylation the salt may be added either before or after removal of the initial solvent and addition of dimethylformamide.

Temperature control is desirably maintained throughout the acylation reaction, which proceeds comparatively rapidly and should normally be complete within one hour. The extent of the acylation may be monitored by, for example, determining the proportion of residual silylated 7-ADCA by paper chromtography, e.g. using a mixture of n-propanol/water (7:3) on Whatman 3 mm paper buffered to pH6.0 with phosphate solution.

We generally prefer in the acylation step to employ a slight excess of phenylglycyl chloride hydrochloride, e.g. 1.05–1.2 equivalents, advantageously about 1.1 equivalents, relative to the quantity of silylated 7-ADCA. The tertiary nitrogen base is preferably employed in amounts of 0.25 to 2 equivalents relative to the quantity of silylated 7-ADCA. Advantageous results may be obtained when pyridine is the tertiary nitrogen base by employing 0.5 equivalents relative to the quantity of silylated 7-ADCA.

After completion of the acylation reaction, for example as evidenced by consumption of the silylated 7-ADCA present, the resulting solution may be treated with a compound containing active hydrogen, e.g. water, acidified or basified water, an alcohol or a phenol, to remove any silyl groups present in the cephalexin reaction product. Lower alcohols such as methanol or ethanol are preferred desilylating agents for this purpose, industrial methylated spirits being a particularly convenient readily available reagent. Insoluble materials present in the reaction mixture, e.g. insoluble salts derived from a hydrogen halide binder employed during silylation, may also conveniently be separated at this stage, for example by filtration or centrifugation.

Thereafter cephalexin may be separated from the reaction mixture as a bis-dimethylformamide solvate in accordance with step (b) of the process by diluting the reaction mixture with water, e.g. by adding 1–2 parts, conveniently about 1.7 parts by volume of water per 10 parts by volume of dimethylformamide, and adjusting the pH of the solution to about 6.9 by addition of base. The base is preferably added portionwise over a period of time, e.g. about 1 hour, a preferred base for this purpose being aqueous ammonia, e.g. 0.880 ammonia solution. The resulting precipitate of cephalexin bis-dimethylformamide solvate, which is relatively free from contamination by 7-ADCA and phenylglycyl chloride hydrochloride by products, may be isolated by conventional techniques such as filtration, centrifugation or decantation.

The bis-dimethylformamide solvate so obtained may, if desired, subsequently be converted to cephalexin, for example by dissolving the solvate in a dilute aqueous solution of a non-oxidising mineral acid, e.g. dilute hydrochloric acid, heating the solution, e.g. to about 60°C, and adding a base, e.g. ammonia or an organic nitrogen base such as triethylamine, to bring about precipitation of cephalexin which may then be isolated, e.g. by filtration. If desired, the mixture may be cooled and/ or treated with a non-solvent for cephalexin, e.g. acetone, prior to isolation of the precipitate in order to enhance the yield of this product. The solid residue so obtained is advantageously dried in vacuo and may then be allowed to equilibrate with water vapour over a period of several hours to yield hydrated cephalexin. Acceptable pharmaceutical grade cephalexin may be isolated using such techniques without the need for any further purification procedures.

The following non-limitative examples serve to illustrate the invention. The N,N-dimethylformamide used in examples 1–5 was dried by standing over molecular sieves, and the acetonitrile by passage down a Woelm basic alumina column. Optical rotations and U.V. spectra were measured on solutions in pH 4.4 buffer (0.08 M aqueous sodium acetate), the former at 0.5% concentration. All temperatures are in degrees Centigrade.

EXAMPLE 1 a. Preparation of Cephalexin bis-dimethylformamide solvate using N,N-dimethylformamide as silylation and acylation solvent To a stirred suspension of 7β-amino-3-methylceph-3-em-4-carboxylic acid (21.4 g, 0.1 mole) in N,N-dimethylformamide (300 ml) at room temperature were added triethylamine (20.5 g, 0.2 mole) and trimethylchorosilane (21.7 g, 0.2 mole). The mixture was stirred without external heating or cooling for 25 minutes and then for a further 5 minutes following the addition of quinoline 1.25 hydrochloride (2.8 g, 0.016 mole containing 0.02 mole hydrogen chloride). The mixture was cooled to −40° and pyridine (8.4 g, 0.106 mole) was added, followed immediately by D(−)α-phenylglycyl chloride hydrochloride (23.2 g, 94% pure, 1.06 molar equivalents) in one charge. The reaction temperature was allowed to rise to −30° where it was maintained for 15 minutes. Dry industrial methylated spirit (IMS-6ml) was added and the mixture was allowed to warm to 0° and was then filtered. The filter bed was washed with N,N-dimethylformamide (50 ml) and the filtrate and wash were combined and diluted with water (60 ml). The solution was mixed well and was adjusted from pH 2.4 to 5.2 using 0.880 ammonia solution. After stirring for 30 minutes with periodic additions of ammonia solution to maintain pH, the mixture was adjusted to pH 6.0. After a further 30 minutes at this pH, the mixture was brought to pH 6.9 where it was stirred at 0° for 15 minutes and the precipitated solid filtered off. The bed was slurry washed with a mixture of N,N-dimethylformamide (100 ml) and water (10 ml) and then with ethyl acetate (100 ml) and ether (100 ml) before being dried in vacuo to constant weight to give cephalexin bis-N,N-dimethylformamide solvate as a white solid (45.8 g, 93% theory); $[\alpha]_D + 103.6°$; $E_{1\ cm}^{1\%}$ (262 nm) 154.

b. Conversion of Cephalexin bis-N,N-dimethylformamide solvate to Hydrated Cephalexin Cephalexin bis-N,N-dimethylformamide solvate [44.67 g, prepared as in Example 1(a)] was dissolved in 93 ml of a mixture of water (110 ml) and concentrated hydrochloric acid (8 ml). The solution was stirred with charcoal (3.0 g) for 5 minutes and filtered through kieselguhr, the remainder of the acid solution being used to wash through the filter. The combined filtrate and wash was heated to 60° and its pH adjusted from 1.6 to 3.6 by addition of triethylamine (12 ml). The mixture was allowed to cool to 50° and acetone (400 ml) was added and the suspension cooled to 0°, at which temperature it was stirred for 15 minutes before filtration. The filter bed was slurry washed with a mixture of acetone (80 ml) and water (20 ml) at 0° and then displacement washed with acetone (2 × 50 ml). The solid was dried in vacuo at 40° for 30 minutes, then left in vacuo at room temperature in the presence of water for 1 hour before leaving overnight in an atmosphere of water vapour to give a white solid, hydrated cephalexin (29.26 g, 87.5% of theory from cephalexin bis-N,N-dimethylformamide solvate) of satisfactory infrared and nuclear magnetic resonance spectra; $[\alpha]_D + 150°$; $E_{1\ cm}^{1\%}$ (262 nm) 227 (to dry); water content 6.2%.

EXAMPLE 2

Preparation of Cephalexin bis-dimethylformamide solvate using acetonitrile as silylation solvent To a stirred suspension of 7β-amino-3-methylceph-3-em-4-carboxylic acid (10.7 g, 0.05 mole) in acetonitrile (150 ml) at room temperature were added triethylamine (10.25 g, 0.1 mole) and trimethylchlorosilane (10.85 g, 0.1 mole). The mixture was stirred for 30 minutes without external heating or cooling and then for a further 20 minutes following the addition of quinoline 1.25 hydrochloride (1.4 g, 0.008 mole containing 0.01 mole hydrogen chloride). The suspension was transferred to an evaporating flask using acetonitrile (100 ml) to wash out the original flask and the reaction mixture and washings were evaporated at 45° in vacuo to give the silyl derivative contaminated with base hydrochlorides, as a pale yellow solid.

The solid isolated above was transferred to a suitable reaction flask as a slurry in N,N-dimethylformamide (50ml) using further N,N-dimethylformamide (100 ml) to complete the transfer.

The suspension was cooled to −50° and, with stirring, pyridine (4.2 g, 0.053 mole) was added, followed immediately by D(−)-α-phenylglycyl chloride hydrochloride (11.6 g, 94% pure, 1.06 molar equivalents) in one charge. The reaction temperature was allowed to rise to −30° where it was maintained for 15 minutes. Dry IMS (3ml) was added and the mixture was allowed to warm to 0° and the precipitated solid filtered off. The filter bed was washed with N,N-dimethylformamide (25 ml) and the filtrate and wash were combined and diluted with water (30 ml). The solution was mixed well and was adjusted from pH 2.4 to 5.2 using 0.880 ammonia solution. After stirring for 30 minutes at pH 5.2, the mixture was adjusted to pH 6.0 where it was kept for 30 minutes before adjusting to pH 6.9 and stirring at 0° for 30 minutes before filtration. The filter bed was slurry washed with a mixture of N,N-dimethylformamide (50 ml) and water (5 ml) and then with ethyl acetate (50 ml) and ether (50 ml) before being dried at 40° in vacuo to constant weight to give cephalexin bis-N,N-dimethylformamide solvate as a creamy white solid (22.0 g, 89% theory); $[\alpha]_D + 106.25°$; $E_{1\ cm}^{1\%}$ (262 nm) 158.

EXAMPLE 3

Preparation of Cephalexin bis-dimethylformamide solvate in N,N-dimethylformamide In a procedure similar to that of Example 1 but omitting quinoline hydrochloride and reducing the pyridine input to 3.93 g (0.05 mole), 7β-amino-3-methylceph-3-em-4-carboxylic acid (22.0 g, 97.4% pure) was converted to cephalexin bis-dimethylformamide solvate (46.17 g, 93.7% theory); $[\alpha]_D + 105.5°$ (c, 1.0%); $E_{1\ cm}^{1\%}$ (262nm) 160.5

EXAMPLE 4

Preparation of Cephalexin bis-dimethylformamide solvate using N,N-dimethylformamide as silylation and acylation solvent and N,O-bis-trimethylsilylacetamide as the silylation reagent To a stirred suspension of 7β-amino-3-methylceph-3-em-4-carboxylic acid (10.7 g, 0.05 mole) in N,N-dimethylformamide (150 ml) at 40° was added N,O-bis-trimethylsilylacetamide (14.1 ml, 87% pure, 0.05 mole). The mixture was stirred for 20 minutes at 40°, then cooled to −40° and pyridine (4.3 ml. 0.053 mole) was added, followed immediately by D(−)-α-phenylglycyl chloride hydrochloride (11.6 g, 94% pure, 0.053 mole) in one charge. The reaction temperature was allowed to rise to −30° where it was maintained for 25 minutes.

The reaction mixture was worked up and the product was isolated as described in Example 1 to give cephalexin bis N,N-dimethylformamide solvate as a white solid (22.35 g, 90.5% theory); $[\alpha]_D + 105.8°$, $E_{1\ cm}^{1\%}$ (262 nm) 162.5.

EXAMPLE 5

Preparation of Cephalexin bis-dimethylformamide solvate using N,N-dimethylformamide as silylation and acylation solvent and N-trimethylsilylacetamide as the silylation reagent To a stirred syspension of 7β-amino-3-methylceph-3-em-4-carboxylic acid (10.7 g, 0.05 mole) in N,N-dimethylformamide (150 ml) at 40° was added N-trimethylsilylacetamide (12.9 g, 0.1 mole). The mixture was stirred for 20 minutes at 40°, cooled to −40° and pyridine (4.3 ml, 0.053 mole) was added, followed immediately by D(−)-α-phenylglycyl chloride hydrochloride (11.6 g, 94% pure, 0.053 mole) in one charge. The reaction temperature was allowed to rise to −30° where it was maintained for 25 minutes.

The reaction mixture was worked up and the product was isolated as described in Example 1 to give cephalexin bis-N,N-dimethylformamide solvate as a white solid (23.15 g, 93.8% theory); $[\alpha]_D + 104.3°$, $E_{1\ cm}^{1\%}$ (262 nm) 163.

EXAMPLE 6

Preparation of Cephalexin bis dimethylformamide solvate in N,N-dimethylformamide using different bases a. α-Picoline: Triethylamine (14.1 ml; 0.1 mole) was added to a stirred suspension of 7β-amino-3-methyl-ceph-3-em-4-carboxylic acid (10.7 g; 0.049 mole) in N,N-dimethylformamide (150 ml) at room temperature followed by trimethylsilyl chloride (12.8 ml; 0.1 mole). After 30 minutes the mixture was cooled to −40° and α-picoline (4.93 g; 0.053 mole) was added followed by α-phenylglycyl chloride hydrochloride (11.6 g; 94% pure, 0.053 mole) in one portion. The temperature was allowed to rise to −30° and there maintained for 30 minutes. Dry industrial methylated spirits (IMS, 3 ml) was added and the reaction mixture allowed to warm to 0° when it was filtered. The cake was washed with N,N-dimethylformamide (25 ml) and the filtrate diluted with water (30 ml). The pH of the filtrate was then adjusted to 6.0 with 0.880 ammonia and thence to 6.9 after 30 minutes stirring at ambient temperature. After cooling to 0° the suspension was stirred at 0° for 15 minutes and filtered. The cake was slurried with 10:1 N,N-dimethylformamide:water (55 ml) and the bed washed by displacement with ethyl acetate (50 ml) and ether (50 ml) and dried in vacuo at 40° to give cephalexin bis dimethylformamide solvate as a white solid (21.2 g, 87.6% theory), $[\alpha]_D + 100.5°$ (c 0.5%), $E_{1\ cm}^{1\%}$ (262 nm) 156.8.

b. N,N-Dimethylaniline: In a procedure similar to that of (a), but replacing α-picoline by N,N-dimethylaniline (12.9 g; 0.106 mole), 7β-amino-3-methyl-ceph-3-em-4-carboxylic acid (10.9 g; 0,050 mole) was converted into cephalexin bis-dimethylformamide solvate (21.0 g; 85.1% of theory), $[\alpha]_D + 101.3°$ (c 0.5%), $E_{1\ cm}^{1\%}$ (262 nm) 157.

c. Quinoline: In a procedure similar to that of (a), but utilising quinoline (6.85 g; 0.053 mole) as base in the coupling reaction, 7β-amino-3-methylceph-3-em-4-carboxylic acid (10.9 g; 0.05 mole) was converted to cephalexin bis-dimethylformamide solvate (20.57 g, 83.5% theory); $[\alpha]_D + 101°$ (c 0.5%); $E_{1\ cm}^{1\%}$ (262 nm) 158.

d. N,N-Diethylaniline: In a procedure similar to that of (a), but utilising diethylaniline (7.91 g; 0.053 mole)

in a coupling reaction lasting 90 minutes at −50°, 7β-amino-3-methylceph-3-em-4-carboxylic acid (10.9 g; 0.05 mole) was converted to cephalexin bis-dimethylformamide solvate (20.70 g; 84.2% theory) $[\alpha]_D + 101°$ (c 0.5%); $E_{1\,cm}^{1\%}$ (262 nm) 162.

We claim:

1. In a process for the preparation of cephalexin the improvement which comprises the steps of (a) contacting a silylated derivative of 7β-amino-3-methylceph-3-em-4-carboxylic acid with phenylglycyl chloride hyrochloride in dimethylformamide at a temperature not exceeding 0°C in the presence of a tertiary nitrogen base having a pKa in the range 3.0–7.0, (b) diluting the dimethylformamide solution with water and adjusting the pH to about 6.9 to precipitate cephalexin bis-dimethylformamide solvate, (c) dissolving the solvate in a dilute aqueous mineral acid solution and heating the solution so formed and (d) contacting the heated solution with ammonia or an organic amine to precipitate cephalexin.

2. A process as defined in claim 1 wherein the tertiary nitrogen base is pyridine.

3. A process as defined in claim 1 wherein said silylated derivative is formed by contacting a dimethylformamide suspension or solution of 7β-amino-3-methylceph-3-em-4-carboxylic acid with a silyl halide.

4. A process as defined in claim 1 wherein the pH is adjusted to about 6.9 by addition of aqueous ammonia.

5. In a process for the preparation of cephalexin the improvement which comprises the steps of dissolving the bis-dimethylformamide solvate of cephalexin in a dilute aqueous mineral acid solution, heating the solution so formed and adding a base selected from the group consisting of ammonia and organic amines thereto to precipitate cephalexin.

6. In a process for the preparation of a bis-dimethylformamide solvate of cephalexin the improvement which comprises the steps of (a) contacting a silylated derivative of 7β-amino-3-methylceph-3-em-4-carboxylic acid with phenylglycyl chloride hydrochloride in dimethylformamide at a temperature not exceeding 0°C in the presence of a tertiary nitrogen base having a pKa in the range 3.0–7.0 and b. diluting the dimethylformamide solution with water and adjusting the pH to about 6.9 to precipitate cephalexin bis-dimethylformamide solvate.

7. A process as defined in claim 6 wherein said silylated derivative is formed by contacting a dimethylformamide suspension or solution of 7β-amino-3-methylceph-3-em-4-carboxylic acid with two molar equivalents of a silyl halide and the resulting silylated derivative is contacted with phenylglycyl chloride hydrochloride at a temperature of from −20° to −40°C in the presence of pyridine.

* * * * *